(12) United States Patent
Drew

(10) Patent No.: US 10,086,064 B2
(45) Date of Patent: Oct. 2, 2018

(54) VACCINE COMPOSITIONS

(71) Applicant: Stabilitech Biopharma Ltd, West Sussex (GB)

(72) Inventor: Jeffrey Drew, Sussex (GB)

(73) Assignee: Stabilitech Biopharma Ltd, Burgess Hill, West Sussex (GB)

( * ) Notice: Subject to any disclaimer, the term of this patent is extended or adjusted under 35 U.S.C. 154(b) by 0 days.

(21) Appl. No.: 15/302,630

(22) PCT Filed: Apr. 8, 2015

(86) PCT No.: PCT/GB2015/051072
§ 371 (c)(1),
(2) Date: Oct. 7, 2016

(87) PCT Pub. No.: WO2015/155527
PCT Pub. Date: Oct. 15, 2015

(65) Prior Publication Data
US 2017/0021008 A1    Jan. 26, 2017

(30) Foreign Application Priority Data
Apr. 11, 2014 (GB) .................... 1406569.2

(51) Int. Cl.
| | | |
|---|---|---|
| *A61K 39/145* | (2006.01) | |
| *A61K 39/39* | (2006.01) | |
| *A61K 31/198* | (2006.01) | |
| *A61K 47/18* | (2017.01) | |
| *A61K 47/26* | (2006.01) | |
| *A61K 9/00* | (2006.01) | |

(Continued)

(52) U.S. Cl.
CPC .......... *A61K 39/145* (2013.01); *A61K 9/0019* (2013.01); *A61K 9/19* (2013.01);
(Continued)

(58) Field of Classification Search
None
See application file for complete search history.

(56) References Cited

FOREIGN PATENT DOCUMENTS

| WO | WO-2011/121301 A1 | 10/2011 |
| WO | WO-2011/121305 A2 | 10/2011 |

(Continued)

OTHER PUBLICATIONS

International Search Report and Written Opinion for PCT/GB2015/051072, dated Jul. 10, 2015 (10 pages).

(Continued)

*Primary Examiner* — Bethany P Barham
*Assistant Examiner* — Barbara S Frazier
(74) *Attorney, Agent, or Firm* — Clark & Elbing LLP; Susan M. Michaud

(57) ABSTRACT

The present invention relates to the use of an excipient which is a compound of formula (I) or a physiologically acceptable salt or ester thereof: wherein: $R_1$ represents $C_{1-6}$alkyl; $R_2$ represents hydrogen or $C_{1-6}$alkyl; and $R_3$ represents $C_{1-6}$alkyl, for increasing the immunogenicity of an influenza antigen, which use comprises (a) freezing, (b) heat-treating, and/or (c) freeze-drying an aqueous composition comprising the influenza antigen and the excipient.

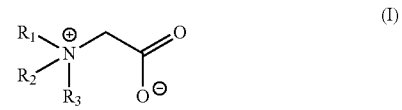

(I)

7 Claims, 3 Drawing Sheets

(51) Int. Cl.
*A61K 9/19* (2006.01)
*A61K 39/12* (2006.01)
*C12N 7/00* (2006.01)
*A61K 39/00* (2006.01)

(52) U.S. Cl.
CPC ............ *A61K 31/198* (2013.01); *A61K 39/12* (2013.01); *A61K 39/39* (2013.01); *A61K 47/186* (2013.01); *A61K 47/26* (2013.01); *C12N 7/00* (2013.01); *A61K 2039/51* (2013.01); *A61K 2039/5252* (2013.01); *A61K 2039/55505* (2013.01); *A61K 2039/55511* (2013.01); *C12N 2760/16134* (2013.01); *C12N 2760/16171* (2013.01)

(56) References Cited

FOREIGN PATENT DOCUMENTS

WO WO-2011/121306 A1 10/2011
WO WO-2013/050780 A1 4/2013

OTHER PUBLICATIONS

Reap et al., "Stimulation of the immune response by dimethylglycine, a nontoxic metabolite," J Lab Clin Med. 115(4):481-6 (1990).
Search Report for UK Application No. GB 1406569.2, dated Nov. 27, 2014 (date of search; 2 pages).
Stabilitech: "Innovations in Health," dated Nov. 19, 2009, internet citation dated Jun. 10, 2010 (21 pages).

VACCINE COMPOSITIONS

FIELD OF THE INVENTION

The invention relates the use of specific dialkylglycine and trialkylglycine excipients to increase the immunogenicity of influenza antigens, as well as to methods for increasing the immunogenicity of influenza antigens, to vaccine compositions obtainable using the method, and to the use of the vaccine compositions in vaccination of patients.

BACKGROUND TO THE INVENTION

Influenza virus is a member of the Orthomyxoviridae family. There are three subtypes of influenza viruses designated A, B, and C that infect humans.

Seasonal epidemics of influenza can spread around the world quickly and inflict a significant economic burden in terms of hospital and other healthcare costs and lost productivity. The World Health Organization estimates that in annual influenza epidemics there are between three and five million cases of severe illness and approximately 250,000 and 500,000 deaths every year around the world.

An influenza pandemic occurs when a new influenza strain emerges in the population with high pathogenicity and antigenic novelty. Global pandemics can afflict between 20% and 40% of the world's population in a single year. The pandemic of 1918-19, for example, affected 200 million people, killing over 30 million worldwide. Although healthcare has dramatically improved since that time, with vaccines and antiviral therapies being developed, it is estimated that a pandemic today would result in two to seven million deaths globally.

In the event that an influenza pandemic were to occur, one problem that could arise is that it might be difficult to manufacture sufficient quantities of the influenza antigens required for use in vaccines in the required timescale. Another problem that could arise is that an influenza vaccines can take several weeks to confer immunity, which may not be quick enough to prevent or reduce the spread of a highly infection strain.

There is therefore a need for influenza antigens with increased immunogenicity, which could be used in smaller quantities and/or confer immunity more quickly than existing antigens.

WO 2011/121301, WO 2011/121306 and WO 2013/050780 are concerned with the use of particular excipients, including dialkylglycines and trialkylglycines such as dimethylglycine (DMG), for stabilising viral particles and/or polypeptides. WO 2011/121305 is concerned with the use of similar excipients for stabilising aluminium salt adjuvant during freezing or drying. None of these references are concerned with increasing the immunogenicity of influenza antigens.

Journal of Laboratory and Clinical Medicine (1990), 115(4), 481-6 by Reap et at describes the immunomodulating capabilities of dimethylglycine (DMG) in a rabbit model. The rabbits were force fed DMG prior to and after inoculation with an influenza antigen. Reap et at does not describe freezing, freeze-drying or heating the influenza antigen in the presence of DMG prior to administration to the rabbits.

SUMMARY OF THE INVENTION

It is a surprising finding of the present invention that that the immunogenicity of influenza antigens can be increased by freezing, freeze-drying or heating the influenza antigen in the presence of dialkylglycines and trialkylglycines such as dimethylglycine (DMG). The resulting modified influenza antigen has increased immunogenicity as compared to the unmodified influenza antigen. The resulting modified influenza antigen also has increased immunogenicity as compared to an influenza antigen which has been mixed with the dialkylglycines/trialkylglycines but has not undergone freezing, freeze-drying or heating.

There are two significant advantages associated with the increased immunogenicity of the modified influenza antigen.

Firstly, the modified influenza antigen can illicit the same immune response in a patient using a much lower dose than unmodified influenza antigen. This "antigen sparing" property is highly advantageous, particularly in a pandemic situation where millions of patients need to be vaccinated.

Secondly, the modified influenza antigen is capable of conferring immunity onto the patient more quickly than the unmodified influenza antigen. The faster onset of immunity is also highly advantageous, particularly in a pandemic situation where it is important to try to stop the spread of the pandemic.

Accordingly, the present invention provides use of an excipient which is a compound of formula (I) or a physiologically acceptable salt or ester thereof:

$$\begin{array}{c} R_1 \diagdown \overset{\oplus}{N} \diagup \diagup \overset{O}{\diagdown} \\ R_2 \diagup \overset{|}{R_3} \quad O^{\ominus} \end{array} \quad (I)$$

wherein:
$R_1$ represents hydrogen or $C_{1-6}$ alkyl;
$R_2$ represents $C_{1-6}$ alkyl; and
$R_3$ represents $C_{1-6}$ alkyl,
for increasing the immunogenicity of an influenza antigen, which use comprises (a) freezing, (b) heat-treating, and/or (c) freeze-drying an aqueous composition comprising the influenza antigen and the excipient.

The invention further provides a method for increasing the immunogenicity of an influenza antigen, said method comprising (a) freezing, (b) heat-treating, and/or (c) freeze-drying an aqueous composition comprising the influenza antigen and an excipient which is a compound of formula (I) or a physiologically acceptable salt or ester thereof:

$$\begin{array}{c} R_1 \diagdown \overset{\oplus}{N} \diagup \diagup \overset{O}{\diagdown} \\ R_2 \diagup \overset{|}{R_3} \quad O^{\ominus} \end{array} \quad (I)$$

wherein:
$R_1$ represents hydrogen or $C_{1-6}$ alkyl;
$R_2$ represents $C_{1-6}$ alkyl; and
$R_3$ represents $C_{1-6}$ alkyl.

The invention further provides a vaccine composition obtainable by said method.

The invention further provides a said vaccine composition, for use in preventing an influenza infection in a human or animal patient.

The invention further provides use of a said vaccine composition in the manufacture of a medicament for preventing an influenza infection in a human or animal patient.

The invention further provides a method of preventing an influenza infection in a human or animal patient, the method comprising administering to said patient a said vaccine composition.

DETAILED DESCRIPTION OF THE INVENTION

Summary

Figure 1:
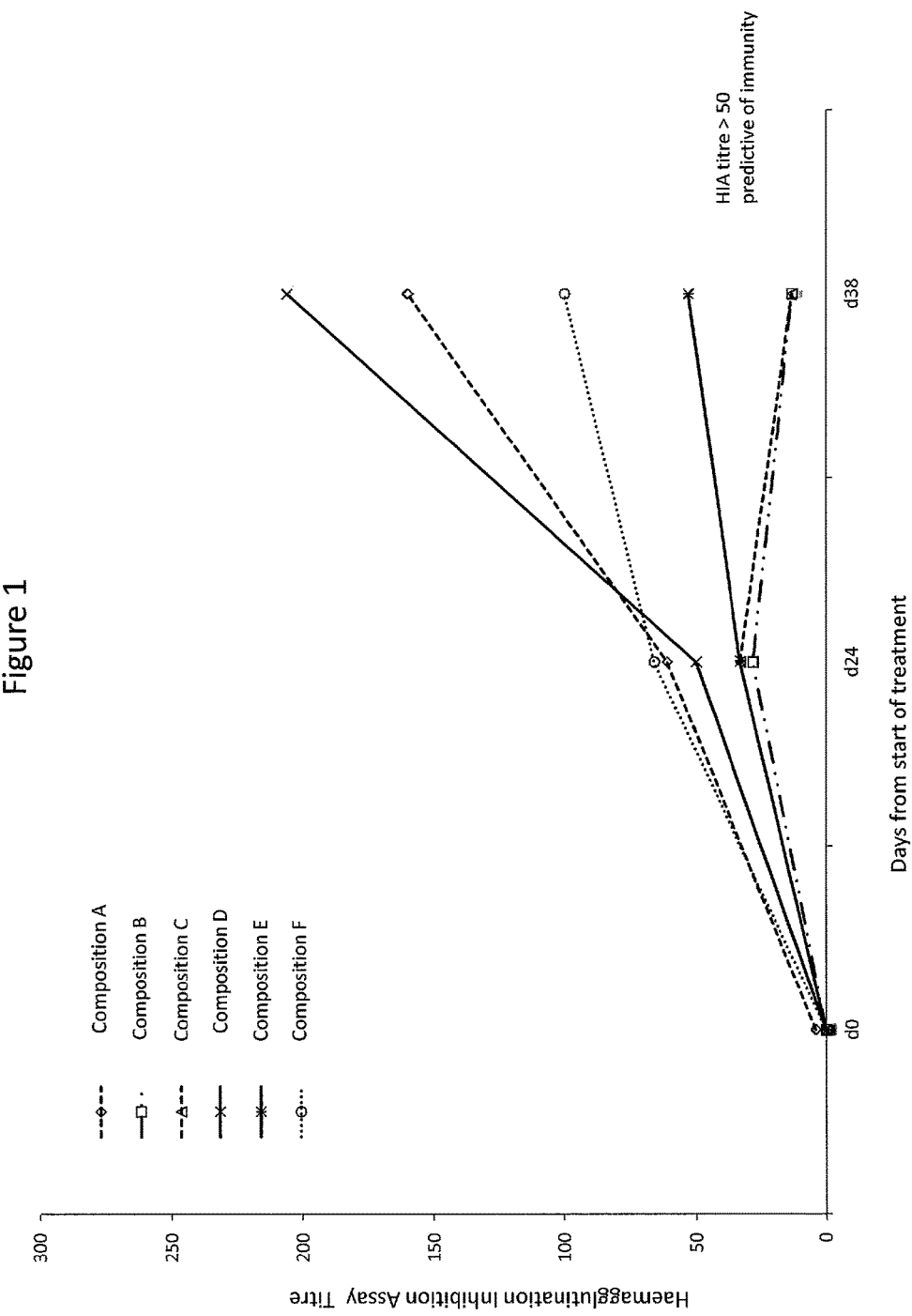
FIG. 1 shows the Haemagglutination Inhibition Assay (HIA) titre measured at various time points for mice administered Compositions A to F at days 1 and 24 in Example 2. Compositions A to C were not been treated with excipient. Composition A contained a normal dose of antigen, whereas Compositions B and C contained 1/100 dose of antigen. Compositions D to F contained 1/100 dose of antigen, but were admixed with excipients and then heat-treated. The HIA titre for Compositions D to F was significantly than that higher observed with control Compositions B and C.

The present invention relates to increasing the immunogenicity of an influenza antigen using excipients of formula (I) or physiologically acceptable salt or ester thereof, such as dimethylglycine.

The influenza antigen is typically admixed with the excipient to give an aqueous composition, and the aqueous composition is then subjected to a treatment, such as freezing, heating and/or freeze-drying, that increases the immunogenicity of the influenza antigen. Freezing, heating and/or freeze-drying the influenza antigen in the presence of the excipient increases the immunogenicity of the antigen as compared to that observed if the influenza antigen is merely mixed with the excipient without freezing, heating and/or freeze-drying.

The influenza antigen and excipient interact during the treatment, thereby to increase the immunogenicity of the influenza antigen, as compared to the immunogenicity of the influenza antigen prior to the treatment. The immunogenicity of the antigen is therefore typically increased during the treatment step.

Typically, the treatment is freezing or heating or freeze-drying, preferably freezing or heating, more preferably freezing. Alternatively, a combination of treatments may be used, such as freezing followed by heating or freeze-drying followed by heating. In the latter case, the freeze-dried composition would typically be reconstituted prior to heating.

The resulting composition can be can be thawed, reconstituted or cooled after freezing, freeze-drying or heating respectively, and administered as a vaccine composition to a patient.

Aqueous Composition

The aqueous composition comprises the excipient and the influenza antigen. The aqueous composition is typically a suspension or solution. The aqueous composition be prepared by admixing the excipient with the influenza antigen in an aqueous solvent. Any suitable aqueous solvent-system may be used. The aqueous solvent may be buffered water. The aqueous solvent is typically HEPES-buffered water, Tris-buffered water, phosphate-buffered water or pure water.

Optionally, one or more sugars is admixed with the aqueous solvent prior to admixture with the excipient and influenza antigen. Alternatively the one or more sugars can be admixed with aqueous solvent after the excipient and influenza antigen.

Optionally, an adjuvant is admixed with the aqueous solvent prior to admixture with the excipient and influenza antigen. Alternatively the adjuvant can be admixed with aqueous solvent after the excipient and influenza antigen.

Typically, if an adjuvant is present, one or more sugars will also be present, since the one or more sugars will generally stabilise the adjuvant, particularly during the treatment step.

Other components may also be present in the aqueous composition. For example, a compound of formula (II) may also be present:

(II)

wherein X represents —S(O)$_2$— and R$_a$ and R$_b$ independently represent C$_{1-6}$ alkyl. A preferred compound of formula (II) is methylsulfonylmethane (MSM) in which R$_a$ and R$_b$ both represent methyl. The combination of excipient and compound of formula (II) may interact together, thereby to further increase the immunogenicity of the influenza antigen during the treatment step.

The concentration of excipient in the aqueous composition is typically in the range of 0.001M or more, preferably in the range of 0.01M or more and more preferably 0.1M or more, for example from 0.1M to 5.0M, or about 0.5M.

If one or more sugar(s) is used, the concentration of sugar or total concentration of sugar in the aqueous composition is typically 1M or less, preferably 0.7M or less, for example 0.5M or less or 0.3M or less. The sugar concentration or the total concentration may be down to 0.1 mM or to 0.5 mM.

The particular concentration of each component that is employed will depend on several factors including the nature of the influenza antigen; the excipient being used; whether one or more sugar is being used and if so the identity of the sugar(s); whether or not an adjuvant is present; and the particular freezing, freeze-drying or heat treatment procedure that is adopted.

The Influenza Antigen

An influenza antigen suitable for use in the invention includes any immunogenic component of an influenza (types A, B or C) vaccine.

The influenza antigen may be a whole inactivated influenza virus or a live attenuated influenza virus. The influenza antigen may be a surface protein of the influenza (types A, B or C). In particular, the influenza antigen may be a hemagglutinin (HA), neuraminidase (NA), nucleoprotein, M1, M2, NS1, NS2(NEP), PA, PB1, PB1-F2 and or PB2 protein, or an immunogenic derivative or fragment of any of these proteins. The influenza antigen may be HA1, HA2, HA3, HA4, HA5, HA6, HA7, HA8, HA9, HA10, HA11, HA12, HA13, HA14, HA15 and/or HA16, any immunogenic fragment or derivative thereof and any combination of the HA proteins, fragments or derivatives. The neuraminidase may be neuraminidase 1 (N1) or neuraminidase 2 (N2).

The Excipient

The excipient is a compound of formula (I) or physiologically acceptable salt or ester thereof.

The physiologically acceptable salt is typically a salt with a physiologically acceptable acid and thus includes those formed with an inorganic acid such as hydrochloric or sulphuric acid or an organic acid such as citric, tartaric, malic, maleic, mandelic, fumaric or methanesulphonic acid. The hydrochloride salt is preferred.

The ester is typically a $C_{1-6}$ alkyl ester, preferably a $C_{1-4}$ alkyl ester. The ester may therefore be the methyl, ethyl, propyl, isopropyl, butyl, isobutyl or tert-butyl ester. The ethyl ester is preferred.

As used herein, a $C_{1-6}$ alkyl group is preferably a $C_{1-4}$ alkyl group. Preferred alkyl groups are selected from methyl, ethyl, propyl, isopropyl, butyl, isobutyl and tert-butyl. Methyl and ethyl are particularly preferred.

For the avoidance of doubt, the definitions of compounds of formula (I) also include compounds in which the carboxylate anion is protonated to give —COOH and the ammonium cation is associated with a pharmaceutically acceptable anion. Further, for the avoidance of doubt, the compounds defined above may be used in any enantiomeric form.

Typically, $R_1$ represents hydrogen or $C_{1-4}$ alkyl, preferably hydrogen or $C_{1-3}$ alkyl, more preferably hydrogen, ethyl or methyl, most preferably hydrogen or methyl.

Typically, $R_2$ represents $C_{1-4}$ alkyl, preferably $C_{1-3}$ alkyl, more preferably ethyl or methyl, most preferably methyl.

Typically, $R_3$ represents $C_{1-4}$ alkyl, preferably $C_{1-3}$ alkyl, more preferably ethyl or methyl, most preferably methyl.

$R_2$ and $R_3$ may be the same or different, but are preferably the same. When $R_1$ represents $C_{1-6}$ alkyl, then $R_1$, $R_2$ and $R_3$ may be the same or different, but are preferably the same.

In a preferred embodiment, $R_1$ represents hydrogen and $R_2$ and $R_3$ are as defined above. Thus, it is particularly preferred that $R_1$ represents hydrogen and $R_2$ and $R_3$ represent methyl, such that the compound of formula (I) is dimethylglycine.

In an alternative preferred embodiment, $R_1$ represents $C_{1-6}$ alkyl and $R_2$ and $R_3$ are as defined above. Thus, it is particularly preferred that $R_1$ to $R_3$ all represent methyl, such that the compound of formula (I) is trimethylglycine.

Alternatively, instead of being a compound of formula (I) or a physiologically acceptable salt or ester thereof, the excipient may be a polymer, such as polyethyleneimine (PEI).

PEI is an aliphatic polyamine characterised by the repeating chemical units denoted as —(CH$_2$—CH$_2$—NH)—. Reference to PEI herein includes a polyethyleneimine homopolymer or copolymer. The polyethyleneimine copolymer may be a random or block copolymer. For example, PEI may consist of a copolymer of polyethyleneimine and another polymer such as polyethylene glycol (PEG). The polyethyleneimine may be linear or branched.

Reference to PEI also includes derivatised forms of a polyethyleneimine. A polyethyleneimine contains nitrogen atoms at various positions. Nitrogen atoms are present in terminal amino groups, e.g. R—NH$_2$, and in internal groups such as groups interrupting an alkyl or alkylene group within the polymer structure, e.g. R—N(H)—R', and at the intersection of a polymer branch, e.g. R—N(—R')—R" wherein R, R' and R" may be alkylene groups for example. Alkyl or aryl groups may be linked to the nitrogen centres in addition to or instead of hydrogen atoms. Such alkyl and aryl groups may be substituted or unsubstituted. An alkyl group would be typically a $C_1$-$C_4$ alkyl group, e.g. methyl, ethyl, propyl, isopropyl, butyl, sec.butyl or tert.butyl. The aryl group is typically phenyl.

The PEI may be a polyethyleneimine that has been covalently linked to a variety of other polymers such as polyethylene glycol. Other modified versions of PEI have been generated and some are available commercially: branched PEI 25 kDa, jetPEI®, LMW-PEI 5.4 kDa, Pseudo-dendrimeric PEI, PEI-SS-PEI, PEI-SS-PEG, PEI-g-PEG, PEG-co-PEI, PEG-g-PEI, PEI-co-L lactamide-co-succinamide, PEI-co-N-(2-hydroxyethyl-ethylene imine), PEI-co-N-(2-hydroxypropyl) methacrylamide, PEI-g-PCL-block-PEG, PEI-SS-PHMPA, PEI-g-dextran 10 000 and PEI-g-transferrin-PEG, Pluronic85®/Pluronic123®-g-PEI. The PEI may be permethylated polyethyleneimine or polyethyleneimine-ethanesulfonic acid.

PEI is available in a broad range of number-average molar masses ($M_n$) for example between 300 Da and 800 kDa. Preferably, the number-average molar mass is between 300 and 2000 Da, between 500 and 1500 Da, between 1000 and 1500 Da, between 10 and 100 kDa, between 20 and 100 kDa, between 30 and 100 kDa, between 40 and 100 kDa, between 50 and 100 kDa, between 60 and 100 kDa, between 50 and 70 kDa or between 55 and 65 kDa. A relatively high $M_n$ PEI of approximately 60 kDa or a relatively low $M_n$ of 1200 Da is suitable.

Preferably, the weight-average molar mass ($M_w$) of PEI is between 500 Da and 1000 kDa. Most preferably, the $M_w$ of PEI is between 500 Da and 2000 Da, between 1000 Da and 1500 Da, or between 1 and 1000 kDa, between 100 and 1000 kDa, between 250 and 1000 kDa, between 500 and 1000 kDa, between 600 and 1000 kDa, between 750 and 1000 kDa, between 600 and 800 kDa, between 700 and 800 kDa. A relatively high $M_w$ of approximately 750 kDa or a relatively low $M_w$ of approximately 1300 Da is suitable.

The weight-average molar mass ($M_w$) and number-average molar mass ($M_n$) of PEI can be determined by methods well known to those skilled in the art. For example, $M_w$ may be determined by light scattering, small angle neutron scattering (SANS), X-ray scattering or sedimentation velocity. $M_n$ may be determined for example by gel permeation chromatography, viscometry (Mark-Houwink equation) and colligative methods such as vapour pressure osometry or end-group titration.

Various forms of PEI are available commercially (e.g. Sigma, Aldrich). For example, a branched, relatively high molecular weight form of PEI used herein with an $M_n$ of approximately 60 kDa and a $M_w$ of approximately 750 kDa is available commercially (Sigma P3143). This PEI can be represented by the following formula:

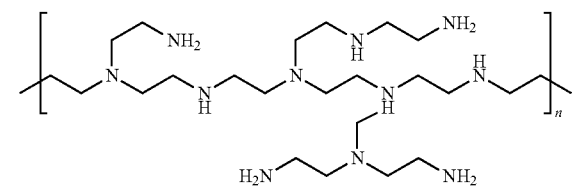

A relatively low molecular weight form of PEI used herein is also available commercially (e.g. Aldrich 482595) which has a $M_w$ of 1300 Da and $M_n$ of 1200 Da.

Sugars

One or more sugars is optionally present in the aqueous composition. Two or more sugars may be present, for example two, three or four sugars. It is preferred that one or two sugars is present, most preferably two sugars. The combination of excipient and sugar(s) may interact together, thereby to increase further the immunogenicity of the influenza antigen during the treatment step. The sugar(s) also assist in stabilising the adjuvant when present, particularly aluminium salt adjuvants, during the treatment step.

The sugar is typically a monosaccharide, a disaccharide, a trisaccharide, a tetrasaccharide, a sugar alcohol or another oligosaccharide.

Typically, the monosaccharide is glucose, fructose, arabinose, glyceraldehydes, galactose or mannose. Typically, the dissaccharide is sucrose, trehalose, lactose, cellobiose, turanose, maltulose, melibiose, isomaltose, or maltose. Typically, the trisaccharide is raffinose, melezitose or umbelliferose. Typically, the tetrasaccharide is stachyose. Typically, the sugar alcohol is mannitol. Other examples of oligosaccharides include the pentasaccharide verbascose.

Typically, the sugar is a non-reducing sugars, for example sucrose or raffinose.

When one sugar is present in the aqueous solution, the sugar is preferably mannitol or sucrose, preferably mannitol.

When two sugars are present in the aqueous suspension, the sugars are preferably sucrose and raffinose.

Adjuvant

An adjuvant is optionally present in the aqueous composition. Any suitable adjuvant may be used, but aluminium salt adjuvants are preferred. When an aluminium salt adjuvant is used, it is preferred that one or more sugars is also present in the aqueous composition, to stabilise the adjuvant during the treatment step.

Typically, the aluminium salt aluminium hydroxide (Al(OH)$_3$), aluminium phosphate (AlPO$_4$), aluminium hydrochloride, aluminium sulphate, ammonium alum, potassium alum or aluminium silicate. Preferably, the aluminium salt adjuvant used is aluminium hydroxide or aluminium phosphate. Most preferably, the aluminium salt adjuvant is aluminium hydroxide (Al(OH)$_3$).

Typically, the aluminium salt adjuvant takes the form of a hydrated gel made from an aluminium salt, the hydrated gel being a particulate suspension in aqueous media. The preparation of aluminium-salt adjuvants are well known to those skilled in the art. For example, aluminium hydroxide and aluminium phosphate adjuvants are generally prepared by exposing aqueous solutions of aluminium ions (typically as sulfates or chlorides) to alkaline conditions in a well-defined and controlled chemical environment, as known to those skilled in the art. Such methods can be used for example, to prepare an aluminium hydroxide or aluminium phosphate hydrated gel.

Freezing

Freezing of the aqueous composition can be conducted by any suitable method. Freezing may thus be carried out by immersing in liquid nitrogen or liquid nitrogen vapour, placing in a freezer or using a dry ice and alcohol freezing bath.

Typically, the aqueous composition is frozen to −4° C. or below, preferably −10° C. or below, more preferably to −20° C. or below, more preferably to −30° C. The aqueous composition is typically not frozen below −100° C. The aqueous composition may, for example, be frozen to about −80° C.

The aqueous composition is typically kept frozen at the desired temperature for 30 minutes or more, preferably 1 hour or more, for example from 2 to 24 hours.

The frozen aqueous composition is typically allowed to thaw by leaving at room temperature before use as a vaccine.

The freezing and thawing conditions can be suitably optimised via routine experimentation.

Freeze-Drying

Freeze-drying can be carried out according to standard procedures. There are three main stages: freezing, primary drying and secondary drying. Freezing is typically performed using a freeze-drying machine. In this step, it is important to cool the biological material below its eutectic point, the lowest temperature at which the solid and liquid phase of the material can coexist. This ensures that sublimation rather than melting will occur in the following steps. Alternatively, amorphous materials do not have a eutectic point, but do have a critical point, below which the product must be maintained to prevent melt-back or collapse during primary and secondary drying.

During primary drying the pressure is controlled by the application of appropriate levels of vacuum whilst enough heat is supplied to enable the water to sublimate. At least 50%, typically 60 to 70%, of the water in the material is sublimated at this stage. Primary drying may be slow as too much heat could degrade or alter the structure of the biological material. A cold condenser chamber and/or condenser plates provide surfaces on which the water vapour is trapped by resolidification.

In the secondary drying process, water of hydration is removed by the further application of heat. Typically, the pressure is also lowered to encourage further drying. After completion of the freeze-drying process, the vacuum can either be broken with an inert gas such as nitrogen prior to sealing or the material can be sealed under vacuum.

The freeze-dried composition is reconstituted as an aqueous composition, using for example water or an aqueous buffer, before use as a vaccine.

The freeze-drying conditions can be suitably optimised via routine experimentation.

Heat Treating

Heating treating of the aqueous composition can be conducted by any suitable method.

Typically, the aqueous composition is heated to greater than 30° C., preferably greater than 40° C. More preferably, aqueous composition is heated to a temperature of 30° C. to 80° C., for example 35° C. to 60° C. or 40° C. to 50° C. A preferred temperature is about 45° C.

Once the aqueous composition has been heated to the desired temperature, is preferably maintained at that temperature for 30 minutes or more, preferably 1 hour or more, for example from 2 hours to 2 weeks or from 4 hours to 24 hours.

A typical heat treatment involves heating to about 45° C. and maintaining at that temperature for about 7 days.

The heat treated aqueous composition is typically allowed to return to room temperature before use as a vaccine.

The heat treatment conditions can be suitably optimised via routine experimentation.

Increase in Immunogenicity

The immunogenicity of the influenza antigen is the ability of that antigen provoke an immune response in the body of a human or animal. A change in immunogenicity can be measured by comparing the immunogenicity of an unmodified (control) influenza antigen with the immunogenicity of an influenza antigen modified in accordance with the invention, using a standard assay for predicting the level of immune response, such as the haemmagglutination inhibition assay.

The immunogenicity of an influenza antigen can be measure using any suitable technique known to those skilled in the art. A preferred standard technique is the haemmagglutination inhibition assay. An exemplary protocol for this assay is set out in the Examples below.

The increased immunogenicity of the modified influenza antigens of the inventions means that the same immune response can be obtained with a smaller amount of modified antigen. Thus, if a patient is administered a dose D of unmodified antigen achieves a level of immunogenicity, then typically a dose of 0.5 D or less, preferably 0.1 D or less, more preferably 0.01 D or less, will achieve the same level of immunogenicity. The immunogenicity is typically measure at least 10 days after administration to the patient, for example after 10 days, 15 days or 20 days.

The increased immunogenicity of the modified influenza antigens of the invention means that the onset of immunity occurs more quickly than with unmodified antigen. Thus, if a patient takes a time T to acquire immunity following administration of a given dose of unmodified antigen, then it will typically take 0.75 T or less time, preferably 0.5 T or less time, most preferably 0.2 T or less time, for a patient administered the same dose of modified antigen to acquire immunity.

Use of Vaccine Compositions

Following freezing, freeze-drying, or heating, the resulting composition can be can be thawed, reconstituted or cooled respectively, and then used as a vaccine composition. The vaccine composition can be diluted as necessary with, for example, phosphate-buffered saline or Water for Injection, prior to use.

Typically, the vaccine composition contains one or more different influenza antigens, at least one of which has been prepared in accordance with the invention. In an embodiment, the vaccine compositions contains two, three or four different influenza antigens, preferably all of which have been prepared in accordance with the invention.

The resulting vaccine composition can then be administered by, for example, injection, to a human or animal patient in need of vaccination. Typically, the patient is a human.

Preferably, the patient is a human who is part of the "at-risk" population. Such patients include children, elderly patients and/or patients suffering from lung diseases, diabetes, cancer, or kidney or heart problems. This patient group is particularly preferred for treatment with the vaccine compositions of the invention, because the rapid onset of immunity achieved with the present vaccines compared to standard vaccines reduces the risk of the patients being infected in the time period between vaccination and onset of immunity.

Preferably, the patient has previously suffered an adverse-reaction to an influenza vaccine. This patient group is particularly preferred for treatment with the vaccine compositions of the invention, because the antigen-sparing effect means that it is necessary to deliver less of the vaccine composition to the patient and accordingly that the risk of an allergic or other adverse reaction to the vaccine is reduced.

The following Examples illustrate the invention.

Example 1—Preparation of Vaccine Compositions

Materials

Dimethylglycine (DMG), sucrose, raffinose, HEPES (4-(2-hydroxyethyl)-1-piperazineethanesulfonic acid) buffer, sodium chloride and sterile water were all used as obtained from a commercial source (Aldrich). Alhydrogel™ was used as obtained from a commercial source (Source Bioscience). Polyethyleneimine (PEI) was used as obtained from a commercial source (Sigma catalogue number: P3143—solution 50% w/v in water; $M_n$ 60,000). Whole inactivated influenza A/Solomon Islands/2006 H1N1 antigen was obtained from the National Institute for Biological Standards and Control (NIBSC).

Composition Preparation 150 ml of HEPES buffer was prepared as follows. 100 ml of sterile water was measured out in a cylinder. 2.5 g NaCl was weighed out on a calibration checked balance and dissolved in the sterile water using a magnetic stirrer and bar. 6 ml of 1M HEPES was added and stirred. When fully dissolved, a pH meter and sodium hydroxide were used to alter the pH to 7.9. The final volume was made up to 150 ml with sterile water. The final HEPES buffer mix was then filtered through a 0.2 μm filter unit in a biological safety cabinet.

After weighing the required excipient components set out in Tables 1 to 3 below, they were placed into a 50 ml sterile flask. Approximately 6 ml of the HEPES buffer was then added to the flask and the contents were mixed by swirling. The flask and contents were then heated in a +60° C. water bath until dissolved. When dissolved, the volume of the mix was measured and the final volume made up to 10 ml with more HEPES buffer. The excipient formulation was filtered through a 0.2 μm filter unit in a biological safety cabinet.

Vials of freeze-dried influenza virus antigen A/Solomon Islands/2006 H1N1 were allowed to reach room temperature from −20° C. and working stocks of the antigen in sterile water were prepared.

Glass screw capped vials (pre autoclaved) were be prepared as detailed in Tables 1 to 3 below. Each vial contain was ultimately to contain total volume of 1 ml. Where required, 500 μl of Alhydrogel™ stock (at a concentration of 2% w/v, to give a final concentration of 1% w/v) was pipetted into each vial. The influenza virus antigen stock was then pipetted into each vial so as to give a final antigen concentration of 2 or 0.2 μg of antigen in each vial. The vials were capped and mixed by vortexing briefly.

The vials were then optionally treated with one of Treatments A to C described below and as set out in Table 1 to 3:

- Treatment 1—the vials were stored at 45° C. for 7 days and then allowed to return to room temperature.
- Treatment 2—the vials were frozen to −80° C. and then allowed to thaw by standing at room temperature.
- Treatment 3—the vials were freeze-dried in a commercial freeze-drier, by freezing to −80° C. and drying for 16 hours under vacuum. The vials were then stored at 45° C. for 7 days and then reconstituted back to a total volume of 1 ml and allowed to return to room temperature.

TABLE 1

| Composition | Influenza antigen | Adjuvant | Excipient | Treatment |
|---|---|---|---|---|
| A | 2 μg | No | None | None |
| B | 0.02 μg | No | None | None |
| C | 0.02 μg | No | None | 1 |
| D | 0.02 μg | Alhydrogel | PEI - 83 μM<br>Sucrose - 73 mM<br>Raffinose - 21 mM | 1 |

TABLE 1-continued

| Composition | Influenza antigen | Adjuvant | Excipient | Treatment |
|---|---|---|---|---|
| E | 0.02 μg | None | PEI - 83 μM<br>Sucrose - 73 mM<br>Raffinose - 21 mM | 2 |
| F | 0.02 μg | Alhydrogel | PEI - 83 μM<br>Sucrose - 73 mM<br>Raffinose - 21 mM | 2 |

TABLE 2

| Composition | Influenza antigen | Adjuvant | Excipient | Treatment |
|---|---|---|---|---|
| G | 2 μg | None | None | None |
| H | 2 μg | None | None | 2 |
| I | 2 μg | None | PEI - 83 μM<br>Sucrose - 73 mM<br>Raffinose - 21 mM | None |
| J | 2 μg | None | PEI - 83 μM<br>Sucrose - 73 mM<br>Raffinose - 21 mM | 2 |
| K | 2 μg | Alhydrogel | None | None |
| L | 2 μg | Alhydrogel | None | 2 |
| M | 2 μg | Alhydrogel | PEI - 83 μM<br>Sucrose - 73 mM<br>Raffinose - 21 mM | None |
| N | 2 μg | Alhydrogel | PEI - 83 μM<br>Sucrose - 73 mM<br>Raffinose - 21 mM | 2 |

TABLE 3

| Composition | Influenza antigen | Adjuvant | Excipient | Treatment |
|---|---|---|---|---|
| O | 2 μg | None | None | None |
| P | 2 μg | None | None | 3 |
| Q | 2 μg | None | PEI<br>Sucrose - 300 mM | 3 |
| R | 2 μg | None | DMG - 275 mM<br>Sucrose - 300 mM<br>MSM - 275 mM | 3 |

Example 2—Antigen Sparing Effect

Compositions A to F prepared in Example 1 were administered subcutaneously to BALB-c mice at day 0 and day 24. The protective effects of the compositions against influenza were determined by measuring the haemmagglutination inhibition assay (HIA) titre of blood taken from the mice at various time points.

The haemmagglutination inhibition assay involved the following steps.
1. Sera was inactivated at 56° C. for 30 minutes.
2. Non-specific chicken red blood cell (CRBC) agglutinating activity was removed by pre-incubation of sera with 1% CRBC for 30 minutes. CRBC was removed and the sera isolated.
3. Sera was serially diluted in PBS/0.5% BSA.
4. HAU of Influenza virus was added to wells.
5. Plates were incubated for 30 minutes at room temperature.
6. 1% CRBC/PBS suspension was added to wells.
7. Plates were incubated for 30-45 minutes at room temperature.
8. Agglutination in wells was determined by eye.
9. HIA titre was recorded and reported, where HIA titre is the reciprocal of the greatest dilution series forming a CRBC pellet.

The results are depicted in FIG. 1. These results for Compositions D to F demonstrate that the combination of excipients with the heat treatment, resulted in an equivalent or better HIA titre compared with the control Composition A. This is unexpected because Compositions D to F contained only 1% by weight of antigen compared to the control (compare with results obtained with Composition B).

Example 3—Acceleration of Onset of Immunity

Compositions G to N prepared in Example 1 were administered subcutaneously to BALB-c mice at day 0 and day 24. The protective effects of the compositions against influenza were determined at various time points by measuring the HIA titre as described in Example 2.

Figure 2:
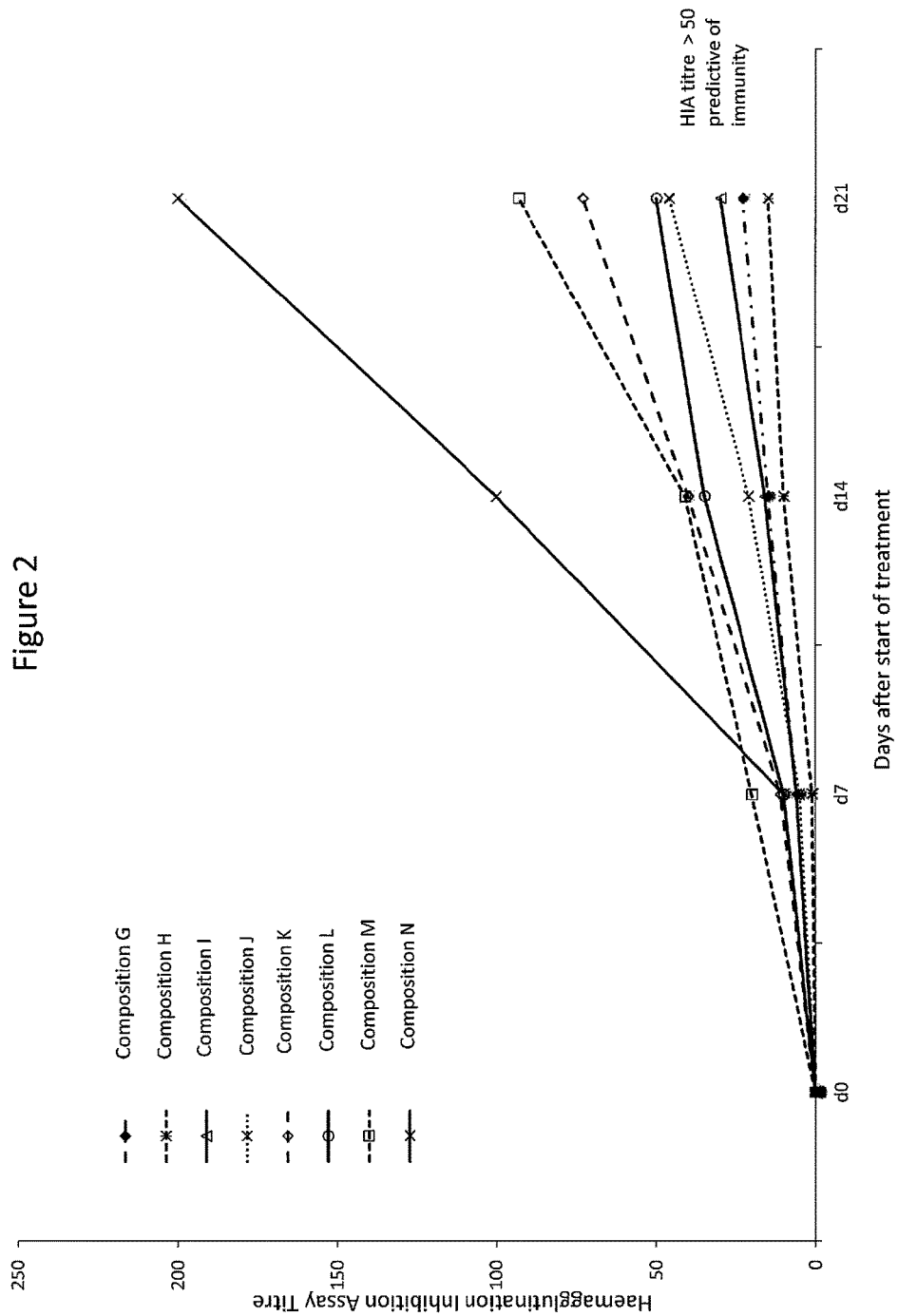
FIG. 2 shows the Haemagglutination Inhibition Assay (HIA) titre measured at various time points for mice administered Compositions G to N at days 1 and 24 in Example 3. The mice were considered to have acquired immunity once the HIA titre was greater than 50. Immunity was acquired most quickly with the combination of excipient, adjuvant and heat treatment (Composition N).

The results are depicted in FIG. 2. The mice were considered to have acquired immunity once the HIA titre was greater than 50. Immunity was acquired most quickly with the combination of excipient, adjuvant and heat treatment (Composition N).

Example 4—Similar Results Observed with Different Excipients

Compositions O to R prepared in Example 1 were administered subcutaneously to BALB-c mice at day 0 and day 21. The protective effects of the compositions against influenza were determined at various time points by measuring the HAI titre as described in Example 2.

Figure 3:
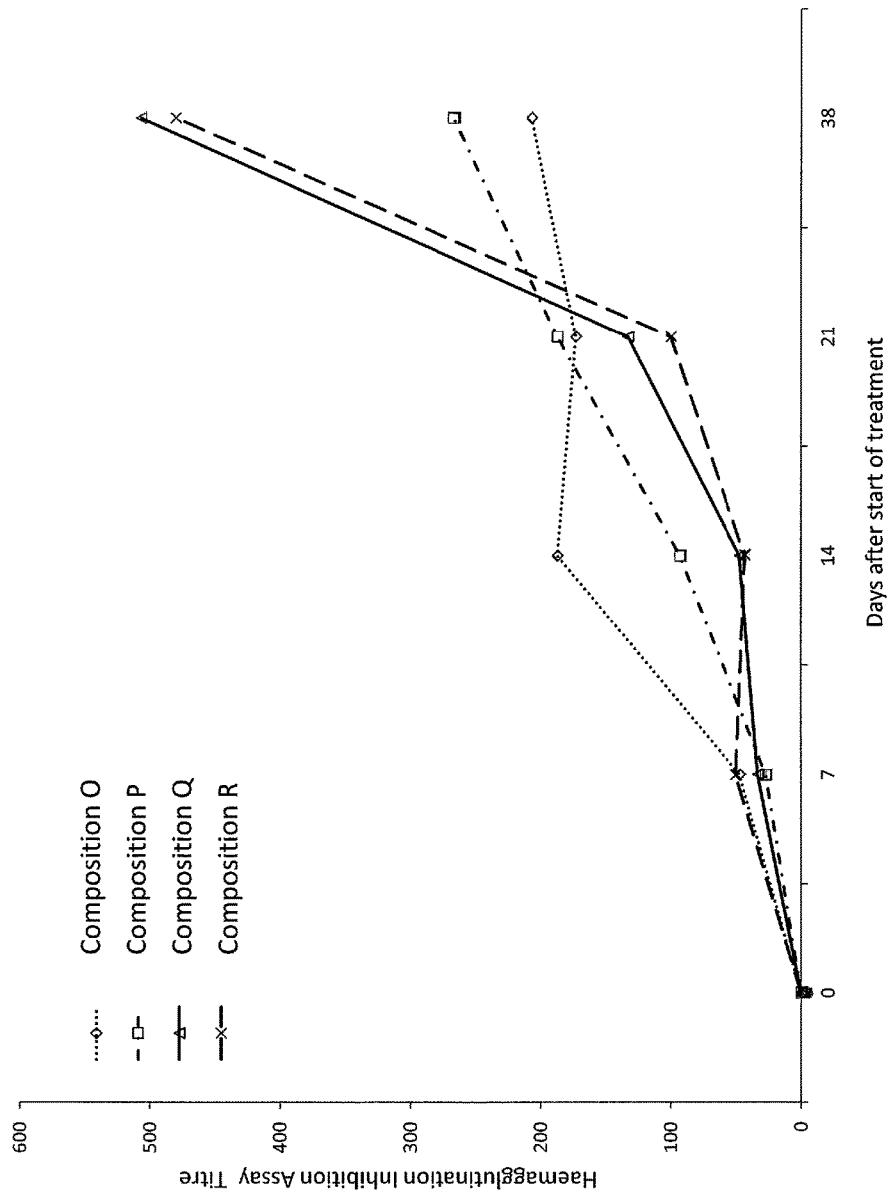
FIG. 3 shows the Haemagglutination Inhibition Assay (HIA) titre measured at various time points for mice administered Compositions O to R at days 1 and 24 in Example 4. These results demonstrate that the effect on influenza antigen observed with polyethyleneimine in Examples 1 and 2 and Composition Q or Example 3 are also observed with dimethylglycine in Composition R of Example 3.

The results are depicted in FIG. 3. These results demonstrate that the effect on influenza antigen observed with polyethyleneimine in Examples 1 and 2 are also observed with dimethylglycine. Thus, the antigen sparing effect and acceleration of onset of immunity observed with polyethyleneimine are also observed with dimethylglycine.

The invention claimed is:

1. A method for increasing the immunogenicity of an influenza antigen, said method comprising heat-treating an aqueous composition at 35° C. to 80° C. for 1 hour or more, the aqueous solution comprising the influenza antigen and an excipient which is a compound of formula (I) or a physiologically acceptable salt or ester thereof:

$$\begin{array}{c} R_1 \\ \diagdown \\ N^{\oplus} \\ R_2 \diagup | \diagdown \\ R_3 \end{array} \diagdown \begin{array}{c} O \\ \diagdown \\ O^{\ominus} \end{array} \quad (I)$$

wherein:

R$_1$ represents hydrogen or C$_{1-6}$ alkyl;

R$_2$ represents C$_{1-6}$ alkyl; and

R$_3$ represents C$_{1-6}$ alkyl; wherein the immunogenicity of the influenza antigen is increased during the heat-treating.

2. The method according to claim 1, in which the compound of formula (I) is dimethylglycine or trimethylglycine.

3. The method according to claim 2, in which the compound of formula (I) is dimethylglycine.

4. The method according to claim 1, in which the aqueous composition further comprises one or more sugars.

5. The method according to claim 4, in which the one or more sugars are sucrose and raffinose.

6. The method according to claim 1, in which the aqueous composition further comprises an adjuvant.

7. The method according to claim 6, in which the adjuvant is an aluminium salt adjuvant.

* * * * *